United States Patent [19]
Sato et al.

[11] Patent Number: 5,597,716
[45] Date of Patent: Jan. 28, 1997

[54] PROCESS FOR PRODUCING D-LACTIC ACID AND L-LACTAMIDE

[75] Inventors: Eiji Sato, Tokyo; Eiji Ozaki; Chinami Iida, both of Otake; Yoshimasa Kobayashi, Tokyo; Akihiro Sakimae, Otake, all of Japan

[73] Assignee: Mitsubishi Rayon Co., Ltd., Tokyo, Japan

[21] Appl. No.: 340,996

[22] Filed: Nov. 17, 1994

[30] Foreign Application Priority Data

| Nov. 18, 1993 | [JP] | Japan | 5-289622 |
| Mar. 7, 1994 | [JP] | Japan | 6-036084 |
| Mar. 7, 1994 | [JP] | Japan | 6-036085 |
| Apr. 15, 1994 | [JP] | Japan | 6-077603 |

[51] Int. Cl.$^6$ ............... C12P 13/02; C12P 7/56; C12P 41/00
[52] U.S. Cl. ............ 435/129; 435/139; 435/280; 435/822; 435/829; 435/840; 435/843; 435/874; 435/876; 435/877
[58] Field of Search ............... 435/129, 139, 435/280, 829, 874, 822, 840, 876, 877, 843

[56] References Cited

FOREIGN PATENT DOCUMENTS

| 61-88894A | 5/1986 | Japan . |
| 62-55098 | 3/1987 | Japan . |
| 2-84198 | 3/1990 | Japan . |
| 3-224496 | 10/1991 | Japan . |

*Primary Examiner*—Herbert J. Lilling
*Attorney, Agent, or Firm*—Pennie & Edmonds

[57] ABSTRACT

The present invention relates to a process for producing D-lactic acid and L-lactamide, comprising allowing a culture broth of a microorganism capable of asymmetric hydrolysis of DL-lactamide belonging to the genus Alcaligenes, Pseudomonas, Agrobacterium, Brevibacterium, Acinetobacter, Corynebacterium, Enterobacter, Micrococcus or Rhodococcus, the microorganism itself, a material obtained therefrom or an immobilized material thereof to act on DL-lactamide, and recovering the resulting D-lactic acid and the remaining L-lactamide. The present invention enables sufficient production of D-lactic acid and L-lactamide by the present microorganism.

29 Claims, 7 Drawing Sheets

FIG.1 Change in conc. with time in the reaction by *Pseudomonas* sp. MR-2301 strain Change in conc. with time in the reaction with 30 weight-% lactamide charged Change in conc. with time in the reaction with 40 weight-% lactamide charged Change in conc. with time in the reaction with 50 weight-% lactamide charged

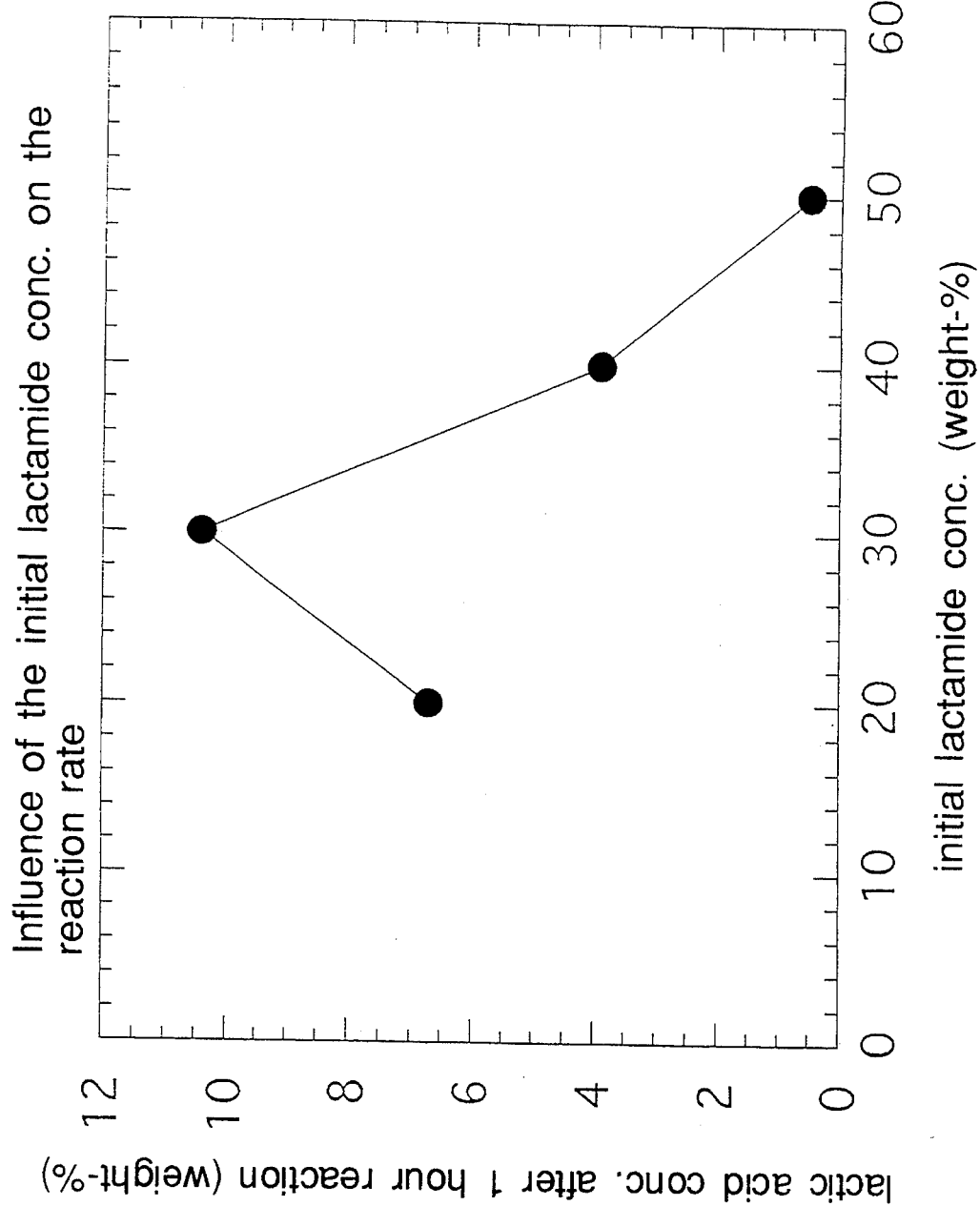

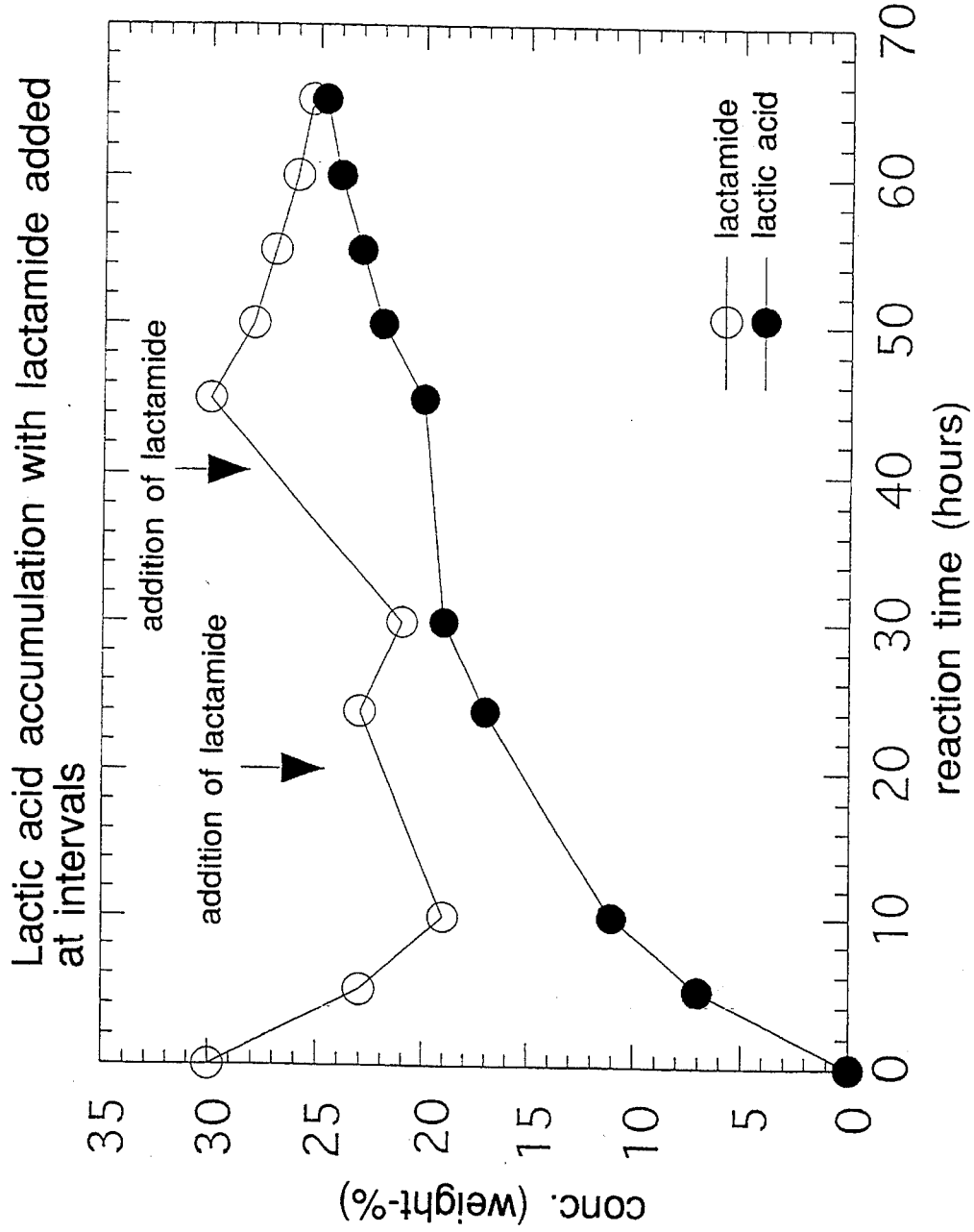

PROCESS FOR PRODUCING D-LACTIC ACID AND L-LACTAMIDE

FIELD OF THE INVENTION

The present invention relates to a process for producing D-lactic acid and L-lactamide by biochemical asymmetric hydrolysis of DL-lactamide. The D-lactic acid obtained in the present invention is a useful compound as a raw material for herbicides based on optically active phenoxypropionic acid or diphenyl ether and for the various pharmaceuticals. Further, it is also expected that the compound can be used as a raw material for biodegradable polymers.

BACKGROUND OF THE INVENTION

Optically active lactic acid has been produced by fermentation using a sugar as the substrate, but such fermentation processes require a considerable long period of time and troublesome operations for the separation, purification, etc. of the lactic acid formed, the concentration of the accumulated product being as low as the level of 10% at best. The production of D-lactic acid by fermentation is disclosed in, e.g. Japanese Laid-Open Patent Application No. 173596/88 and Japanese Patent Publication No. 38593/93.

For the enzymatic production of lactic acid, mention may be made of the production of an optically active α-substituted organic acid from a nitrile as the starting material (Japanese Laid-Open Patent Application Nos. 84198/90 and 224496/91) and the production of optically active lactic acid (Japanese Laid-Open Patent Application Nos. 99497/92 and 219987/93).

As other known processes, mention may be made of the production of an optically active -hydroxycarboxylic acid from an α-hydroxymethyl ester as the starting material (Japanese Patent Publication No. 63397/88), the production of an optically active α-hydroxcarboxylic acid (Japanese Laid-Open Patent Application No. 156892/90), the production of optically active lactic acid from 2-halogenopropionic acid (Japanese Laid-Open Patent Application No. 31690/84), the production of D-lactic acid from 1,2-propanediol (Japanese Laid-Open Patent Application No. 271787/92).

As processes using an amide as the starting material, mention may be made of the production of optically active α-oxyacid by a microorganism (Japanese Laid-Open Patent Application No. 88894/86), the production of optically active α-oxyacid (Japanese Laid-Open Patent Application No. 55098/87), the production of an optically active α-substituted organic acid (Japanese Laid-Open Patent Application No. 84198/90) and the production of an optically active α-substituted organic acid (Japanese Laid-Open Patent Application No. 224496/91).

Japanese Laid-Open Patent Application Nos. 88894/86, 84198/90 and 224496/91 suggests a possibility of converting a racemic amide into the corresponding optical active carboxylic acid in a general description without providing any specific example for direct production of optically active lactic acid from DL-lactamide, and it is not clear whether optically active lactic acid can be produced directly from DL-lactamide. Japanese Laid-Open Patent Application No. 88894/86 merely discloses a process in which only 2 kinds of microorganisms are used for the conversion of a specific α-hydroxyamide into the corresponding optically active α-hydroxycarboxylic acid. Japanese Laid-Open Patent Application Nos. 84198/90 and 224496/91 are directed to processes for converting an α-substituted nitrile or α-substituted amide into the corresponding α-substituted acid by a microbial enzyme reaction. However, this prior art does not contain any description of the production of D-α-substituted acid, such as lactic acid having a combination of hydroxyl group and low molecular weight alkyl group because all the products exemplified for the production of an αsubstituted acid from an -substituted amide are those having halogen, aryl group, aryloxy group, heterocyclic group, etc., bound to the optically active carbon, with the majority of the exemplified processes being related to another process for producing an optically active α-substituted acid from an α-substituted nitrile.

Japanese Laid-Open Patent Application No. 55098/87 discloses a process for producing L-lactic acid from DL-lactamide, but there is still not known any process for producing a predominant amount of D-lactic acid from DL-lactamide.

In addition, none of the above prior art refers to the efficient utilization of an enzyme and microorganism in each reaction.

Further, in the above prior art there does not appear any particular description with respect to the concentration of the optically active substance accumulated, the concentration if any being only a few % or less in a few examples.

The efficient utilization of an enzyme and microorganism and the accumulation of a high concentration of D-lactic acid and L-lactamide therefore have been an important task for the industrial production of both the compounds.

SUMMARY OF THE INVENTION

The present inventors arrived at the present invention as result of their eager research on the direct production of a predominant amount of D-lactic acid and L-lactamide from DL-lactamide as the starting material.

That is, the present invention relates to a process for producing D-lactic acid and L-lactamide, comprising allowing a culture broth of a microorganism capable of asymmetric hydrolysis of DL-lactamide belonging to the genus Alcaligenes, Pseudomonas, Agrobacterium, Brevibacterium, Acinetobacter, Corynebacterium, Enterobacter, Micrococcus or Rhodococcus, the microorganism itself, a material obtained therefrom or an immobilized material thereof to act on DL-lactamide.

The present invention further relates to a process for producing D-lactic acid comprising allowing a culture liquid of the microorganism, the microorganism itself, a material therefrom or an immobilized material thereof to act on DL-lactamide and recovering the resulting D-lactic acid. The present invention also relates to a process for producing L-lactamide comprising allowing a culture broth of the microorganism, the microorganism itself, a material therefrom or an immobilized material thereof to act on DL-lactamide and recovering the remaining L-lactamide.

BRIEF DESCRIPTION OF THE DRAWINGS

FIG. 6 shows the influence of the initial concentration of lactamide on the reaction rate of lactic acid formation.

FIG. 7 shows the accumulation with time of lactic acid where lactamide was added at intervals.

DETAILED DESCRIPTION OF THE INVENTION

Figure 1:
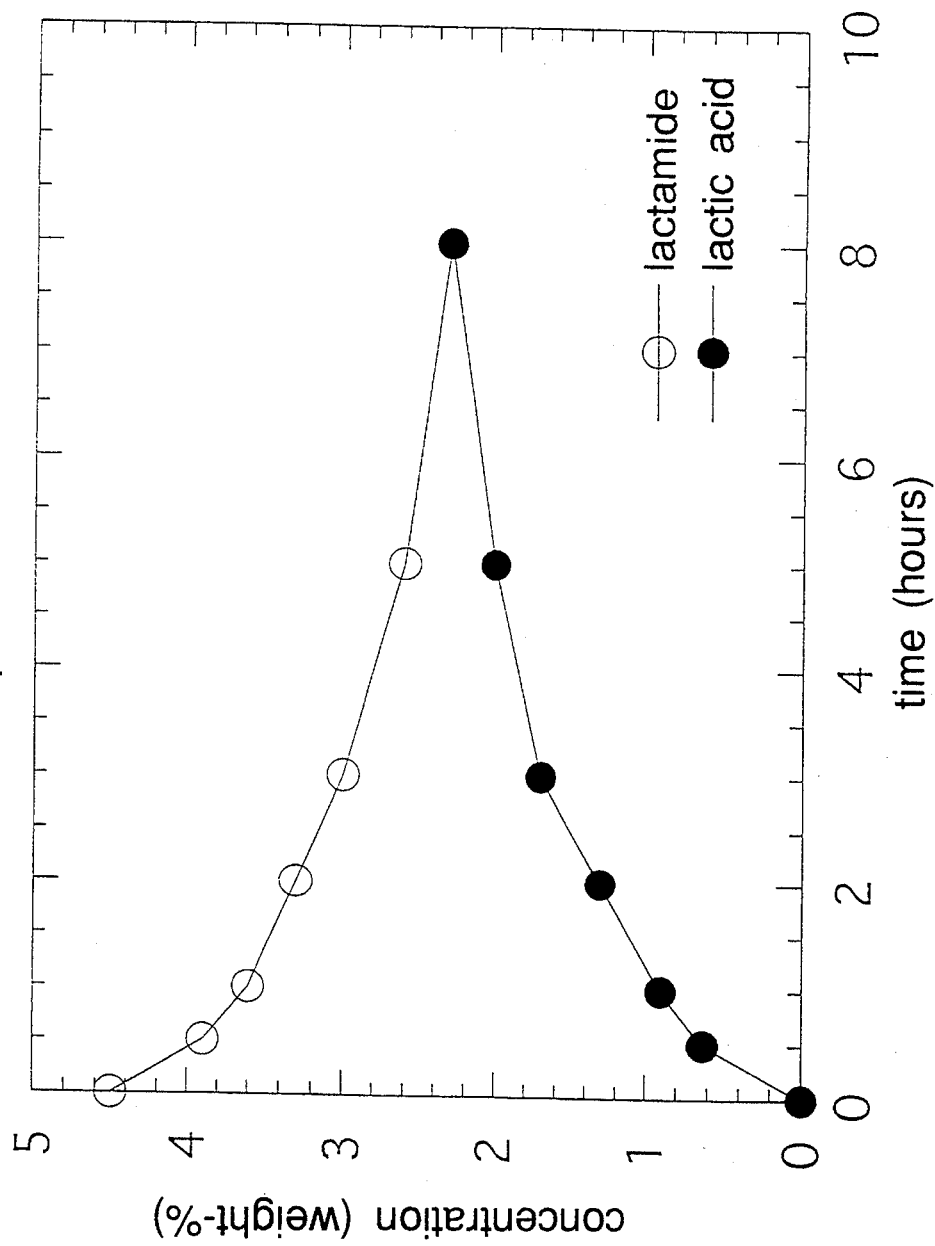
FIG. 1 shows the change with time in the concentrations of the starting material lactamide and the product lactic acid by Pseudomonas sp. MR-2301 strain.

The microorganism used in the present invention is not particularly limited insofar as it is capable of asymmetric hydrolysis of DL-lactamide into D-lactic acid and L-lactamide, belonging to the genus Alcaligenes, Pseudomonas, Agrobacterium, Brevibacterium, Acinetobacter, Corynebacterium, Enterobacter, Micrococcus or Rhodococcus. Examples of microorganisms are Alcaligenes sp. MR-2201 strain (FERM BP-4869), Alcaligenes *faecalis* IFO13111, *Pseudomonas* sp. MR-2301 strain (FERM BP4870), Pseudomonas putida IFO12996, *Pseudomonas fluorescens* IFO3903, *Agrobacterium* tumefaciens IAM1037, *Agrobacterium tumefaciens* ATCC4720, *Agrobacterium radiobacter* IFO12607, *Agrobacterium radiobacter* IAM1526, *Brevibacterium ammoniagenes* IFO12072, *Brevibacterium ammoniagenes* IAM1645, *Acinetobacter* sp. MR-2302 strain (FERM BP-4871), *Corynebacterium nitrilophilus* ATCC21419, *Enterobacter cloacae* IFO3320, *Micrococcus varians* IAM1099, *Micrococcus luteus* IFO12708, *Rhodococcus equi* IFO3730, *Rhodococcus equi* IFM152 *Rhodococcus erythropolis* IFM155, *Rhodococcus erythropolis* IFO12320, *Rhodococcus erythropolis* IFO12538 and *Rhodococcus rhodnii* IFM148.

Among them, preferably used are Alcaligenes sp. MR-2201 strain (FERM BP-4869), Pseudomonas sp. MR-2301 strain (FERM BP4870) and Acinetobacter sp. MR-2302 strain (FERM BP-4871).

Alcaligenes sp. MR-2201 strain, Pseudomonas sp. MR-2301 strain and Acinetobacter sp. MR-2302 strain, newly isolated from soil by the present inventors, have been deposited. On Apr. 7, 1994, Applicants deposited with the National Institute of Bioscience and Human-Technology, Agency of Industrial Science and Technology, Japan, a bacterial strain described herein as Acinetobacter sp. MR-2302, under accession number FERM BP-4871. On Nov. 8, 1993, Applicants deposited with the National Institute of Bioscience and Human-Technology, Japan, bacterial strains described herein as Alcaligenes sp. MR-2201 and Pseudomonas sp. MR-2301, under accession number FERM BP-4869 and FERM-BP 4870, respectively. As of Nov. 2, 1994, these deposits are in accord with the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by the National Institute of Bioscience and Human-Technology, Agency of Industrial Science and Technology, Japan, under the terms of the Budapest Treaty, and subject to an agreement between Applicants and the National Institute of Bioscience and Human-Technology, Agency of Industrial Science and Technology, Japan, which assures unrestricted availability upon issuance of the pertinent U.S. patent. Availability of the deposited strains is not to be construed as a license to practice the invention in contravention of the rights granted under the authority of any government in accordance with its patent laws. Their bacterial characteristics are as follows:

| MR-2201 strain | |
|---|---|
| cell shape | rod-shaped bacillus |
| Gram stain | − |
| spore | − |
| motility | + |
| flagella | surrounding flagella |
| oxidase | + |
| catalase | + |
| attitude toward oxygen | aerobic |
| O-F test (Hugh-Leifson method) | − |
| quinone type | Q-8 |
| MR-2301 strain | |
| cell shape | rod-shaped bacillus |
| Gram stain | − |
| spore | − |
| motility | + |
| flagella | polar flagella |
| oxidase | + |
| catalase | + |
| attitude toward oxygen | aerobic |
| O-F test | 0 |
| quinone type | Q-8 |
| assimilation of methanol | − |
| growth at pH 3.6 | − |
| MR-2302 strain | |
| cell shape | short rod-shaped bacillus |
| Gram stain | − |
| spore | − |
| motility | − |
| oxidase | − |
| catalase | + |
| attitude toward oxygen | aerobic |
| OF test | − |
| GC content (mole-%) | 38 |

When classified on the basis of Bergey's Manual of Systematic Bacteriology (1986), the strains Alcaligenes sp. MR-2201, Pseudomonas sp. MR-2301 and Acinetobacter sp. MR-2302 were identified as falling under the genera Alcaligenes, Pseudomonas and Acinetobacter, respectively.

In the present invention, one of these strains is usually used, but a combination of two or more different microorganisms having the same ability can also be used.

Further, the present inventors made an extensive examination of a process for efficiently producing D-lactic acid and L-lactamide. In this examination, the present inventors first attempted immobilization of the above enzyme-containing microorganism capable of asymmetric hydrolysis of DL-lactamide by inclusion into an acrylamide polymer gel for the purpose of the application of said microorganism to hydrolysis. The immobilization method using an acrylamide polymer gel has been well elucidated (e.g. "Hakko To Kogyo" (Fermentation and Industry), Vol. 35, No. 3, pp. 281–293 (1977)), and in such a method, an enzyme is included in a gel by polymerization with acrylamide.

However, this method has a problem in that as the immobilized microorganism is repeatedly used, its activity is significantly lowered and the gel is destroyed when being suspended.

The present inventors found that the problem of the decrease in activity results from the leakage of the enzyme separated from the microorganism into the reaction solution. As an approach to prevent such leakage from the gel network structure, the prior art teaches the treatment of the enzyme molecule with a polyfunctional crosslinking agent for attaining a further higher molecular weight (e.g. Japanese Patent Publication No. 36959/83).

If the enzyme is to be chemically modified with a crosslinking agent as described in the prior art, it is necessary to select a crosslinking agent so as not to impair the enzyme activity. However, the impairment of the enzyme activity inevitably results from the treatment for stable crosslinking of the enzyme with any conventional crosslinking agent. This also applies to the enzyme capable of forming D-lactic acid and L-lactamide by biochemical asymmetric hydrolysis of DL-lactamide, and it is necessary to find a crosslinking agent and conditions suitable for the enzyme.

To solve the problem, the present inventors found that an enzyme-containing microorganism capable of forming D-lactic acid and L-lactamide by biochemical asymmetric hydrolysis of DL-lactamide or a material derived from said microorganism can be immobilized with stability and without any loss in activity by adding a polyfunctional crosslinking agent containing aldehyde groups and an entrapping material containing an acrylamide monomer to said microorganism or a material therefrom, followed by polymerization thereof, and forming the resulting polymer into an arbitrary shape. The present inventors further found that the microorganism capable of forming D-lactic acid and L-lactamide by asymmetric hydrolysis of DL-lactamide can be repeatedly used in a suspension with less disruption and without any enzyme leakage by allowing said microorganism, said polyfunctional crosslinking agent and said entrapping material to be homogeneously mixed and polymerized in a specific ratio, typically 1: 0.01–0.25: 0.5–10 by weight.

For the production of a high concentration of D-lactic acid and L-lactamide from DL-lactamide as the starting material, the present inventors further examined the influence of several factors on hydrolysis. As a result, they found that although D-lactic acid and L-lactamide can substantially not be produced owing to a significantly lowered reaction rate in the presence of 40 weight-% or more DL-lactamide in the reaction system, the product can be accumulated under the control of the concentration of DL-lactamide.

That is, the present inventors found that D-lactic acid and L-lactamide can be accumulated respectively at a concentration as high as 10 weight-% or more in the presence of DL-lactamide adjusted in the range of up to 40 weight-% in the reaction system during the formation of D-lactic acid and L-lactamide from DL-lactamide by the action of a culture broth of the microorganism capable of asymmetric hydrolysis of DL-lactamide, the microorganism itself, a material obtained therefrom or an immobilized material thereof.

Hereinafter, the general embodiment of the present invention is described.

1) Preparation of the microorganism

The microorganism for use in the present invention is cultured in a medium containing an amide such as lactamide or propionamide or a derivative thereof as the sole carbon and nitrogen source; a combination of the above amide as the nitrogen source and a carbon source; or a combination of a carbon source and nitrogen source, the carbon or nitrogen source containing an inorganic nutrient source required for the growth of the microorganism.

For example, the carbon source includes glycerol, glucose, sucrose, etc.; the nitrogen source includes yeast extract, peptone, ammonium sulfate, etc.; and the inorganic nutrient source includes phosphate, sodium salt, potassium salt, magnesium salt, iron salt, manganese salt, zinc salt, etc.

Cultivation is effected for 1–7 days at pH 4–10 at a temperature of 20°–50° under aerobic conditions.

An amide such as lactamide, propionamide, etc., or a derivative thereof, can be added as an enzyme inducer at the initial to the middle stage of the cultivation to achieve a higher enzyme activity.

The resulting culture broth, the microorganism itself or a material obtained therefrom (disrupted microorganism, crude or purified enzyme, immobilized microorganism or enzyme, etc.) may be used for the reaction.

The immobilization of the microorganism is described below in detail.

2) Preparation of the immobilized microorganism

The crosslinking agent used in the present invention is polyfunctional one with aldehyde groups. This crosslinking agent refers to a compound containing two or more aldehyde groups in one molecule. Examples are glutaraldehyde, glyoxal, etc., and a mixture thereof, among which glutaraldehyde is preferably used.

The entrapping material used in the present invention is one containing an acrylamide type monomer. This entrapping material refers to a compound capable of gelation by polymerization to include the microorganism.

Examples of acrylamide type monomers are acrylamide, methacrylamide, N,N-methylene-bis-acrylamide, etc., and a suitable combination thereof is preferably used.

An ethylene type unsaturated monomer copolymerizable with the acrylamide type monomer may be additionally used for firmly immobilizing the microorganism on the polymer. Examples of ethylene type unsaturated monomers are dimethylaminoethyl methacrylate, diethylaminoethyl methacrylate, dimethylaminopropyl methacrylate and diethylaminopropyl methacrylate or quaternary derivatives thereof, preferably used in a suitable combination thereof.

To use the ethylene type unsaturated monomer in combination, this monomer is employed in the range of 0.01–0.5 part, preferably 0.05–0.2 part, relative to 1 part of the acrylamide type monomer by weight.

The crosslinking agent, the entrapping material and the microorganism as described above are homogeneously mixed in an aqueous medium. Preferably, the crosslinking agent is used in the range of 0.01–0.25 part and the entrapping material in the range of 0.5–10 parts relative to 1 part of the microorganism by weight. A lower amount of the crosslinking agent is not preferred because insufficient immobilization leads to the leakage of the microorganism. A higher amount of the crosslinking agent is not preferable either because a mechanically strong gel is hard to obtain due to the inhibition of the polymerization of the entrapping material. Further, the amount of the entrapping material also highly affects the strength of the polymer gel and the activity of the enzyme: that is, the insufficient immobilization of the microorganism results from a lower amount of entrapping material and the insufficient expression of the enzyme activity from a higher amount of entrapping material. It is particularly preferred that the crosslinking agent is used in the range of 0.03–0.2 part and the entrapping material in the range of 0.8 to 8 parts relative to 1 part of the microorganism by weight.

As the aqueous medium, mention may be made of water, physiological saline, phosphate buffer, etc., or a mixture system based thereon containing a suitable amount of organic solvent etc. The organic solvent includes, but is not limited to, methanol, ethanol, dimethylformamide, dioxane, etc.

The aqueous medium is used preferably in the range of 1–50 parts, more preferably 2–10 parts, relative to 1 part by weight of the crosslinking agent and the entrapping material in total.

A stirrer equipped with a propeller, a homogenizer, etc. are preferably used to make a mixture.

The resulting mixture is polymerized using a polymerization initiator. The polymerization initiator is not particularly limited and a redox type initiator such as potassium persulfate or ammonium persulfate is preferably used. The polymerization initiator is used preferably in the range of 0.0001–0.1 part, more preferably 0.0005–0.01 part, relative to 1 part of the mixture by weight (excluding the aqueous medium).

For the promotion of polymerization, a polymerization promoter such as dimethylaminopropionitrile, triethanolamine, etc., may also be used. The polymerization promoter is preferably used in the range of 0.0001–0.1 part, more preferably 0.0005–0.01 part, relative to 1 part of the mixture by weight (excluding the aqueous medium). The polymerization promoter may be previously added in the former mixing step.

Regardless of which additives are added, the microorganism is maintained in the range of 0.1–50 weight-%, preferably 1–20 weight-% in the polymerization system.

Although polymerization conditions are not particularly limited, preferably used are the range of pH 5–10, preferably pH 6–8 and the temperature range of −10 to +30° C., more preferably 0° to 20° C. An oxygen-free atmosphere such as a nitrogen atmosphere is preferably used to permit polymerization to proceed smoothly. The polymerization is conducted usually for 10 seconds to 10 hours.

After the conclusion of the polymerization, the resulting polymer containing the microorganism immobilized is subjected to molding. The shape is not particularly limited, usually granules being spherical, cylindrical, polygonal or the like. To facilitate the recovery of the product from the reaction solution and the higher expression of the enzyme activity, etc., the particle diameter is preferably 0.1–2 mm, more preferably 0.5–1 mm.

The molding means is not particularly limited. One example involves extruding the resulting polymer through a chopper (wire mesh) and cutting it off with a cutting knife.

In the immobilized microorganism obtained in the manner as described above, it is assumed that the enzyme is included in the acrylamide type polymer gel by crosslinking with the polyfunctional crosslinking agent containing aldehyde groups.

3) Asymmetric hydrolysis

D-lactic acid and ammonia are formed upon rapid hydrolysis in the presence of DL-lactamide in an aqueous medium containing the culture liquid obtained above, the microorganism itself, or a material therefrom (disrupted microorganism, crude or purified enzyme, immobilized microorganism or enzyme, etc.).

The concentration of DL-lactamide in the reaction system is not particularly limited, usually 0.01 to 60 weight-% being preferable. Hydrolysis proceeds rapidly and efficiently in the presence of DL-lactamide adjusted in the range of 40 weight-% or less, preferably 5–30 weight-%, in an aqueous medium containing the microorganism or a material therefrom (disrupted microorganism, crude or purified enzyme, immobilized microorganism or enzyme, etc.), whereby D-lactic acid and L-lactamide can be rapidly accumulated at a high concentration of 10 % or more and even 20 weight-% or more.

In the present invention, it is necessary for the concentration of DL-lactamide in the reaction system to be controlled in the range of 40 % or less for the duration of the reaction from the start to the end. In the presence of 40 weight-% or more DL-lactamide, the reaction rate drops, presumably resulting from the inactivation of the enzyme. DL-lactamide may be supplied continuously or at intervals in the range of up to 40 weight-% preferably up to 30 weight-% so as to compensate for the DL-lactamide consumed in the reaction. Alternatively, no additional DL-lactamide needs to be added during the reaction after DL-lactamide was initially mixed in the range of up to 40 weight-%. D-lactic acid and L-lactamide can be accumulated at a concentration as high as 10 weight-% or more in the presence of DL-lactamide adjusted as described above.

In the reaction system, there is no particular limitation made to the content with respect to a culture of the microorganism, the microorganism itself or a material therefrom. However, if the microorganism itself is used, it is preferably used in the range of 0,001–10 weight-%, more preferably 0.01–2 weight-%, in terms of dried microorganism. If the immobilized microorganism is used, it is preferably used in the range of 0.01–10 weight-%.

The reaction conditions are not particularly limited. However, the reaction is usually carried out for stable enzyme activity in the range of pH 3–12 preferably pH 5–9 at a temperature of 5°–70° C., preferably 10°–50° C., and for 0.5–120 hours, preferably 5–24 hours.

The remaining L-lactamide may be isolated for use in subsequent chemical hydrolysis into L-lactic acid. Hence, the present invention enables the production of both D- and L-lactic acid in a series of operations.

The microorganism or enzyme immobilized according to a conventional method may be used in the above reaction. Any of the batch, continuous and reuse system can be used for the reaction.

The separation of the optically active lactic acid from the reaction solution can be effected by centrifugation, filtration, etc. and subsequent subjection to conventional steps such as extraction, ion-exchange, electrodialysis, etc.

EXAMPLES

The present invention is described in more detail with the following examples, which however are not intended to limit the scope of the invention.

Example 1

Alcaligenes sp. MR-2201 strain was cultivated at 30° C. for 48 hours under shaking in a culture medium of the following composition.

| Medium Composition | |
|---|---|
| peptone | 16 g |
| yeast extract | 10 g |
| sodium chloride | 5 g |
| lactamide | 1 g |
| water | 1000 ml |

Then, the microorganism was harvested from the culture broth by centrifugation and washed with 0.05M phosphate buffer, pH 7. After the cell concentration was adjusted to 2 weight-% in terms of dried microorganism, and DL-lactamide was adjusted to 5 weight-% in the buffer, they were allowed to react at 30° C. The DL-lactamide and lactic acid formed were analyzed by high performance liquid chromatography (HPLC). In the reaction for 40 hours, D-lactic acid (100% e.e.) was formed in approx. 100 mole-% yield from D-lactamide. Their optical purity was analyzed by Chiralpak WH column supplied by Daicel Chemical Industries, Ltd.

Example 2

Alcaligenes faecalis IFO13111 strain was cultivated at 30° C. for 48 hours under shaking in the culture medium shown in Example 1. Then, the microorganism was harvested from the culture broth by centrifugation and washed with 0.D5M phosphate buffer, pH 7. After the cell concentration and DL-lactamide were adjusted respectively to approx. 10 weight-% and 2 weight-% in the buffer, they were allowed to react at 30° C. The DL-lactamide present and the lactic acid formed were analyzed by HPLC. In the reaction for 18 hours, D-lactic acid (60% e.e.) was formed in almost 100 mole-% yield from D-lactamide.

Example 3

Pseudomonas sp. MR-2301 strain was cultivated at 30° C. for 48 hours under shaking in the culture medium shown in Example 1. Then, the microorganism was harvested from the culture broth by centrifugation and washed with 0.05M phosphate buffer, pH 7. After the cell concentration was adjusted to 2 weight-% in terms dried microorganism and DL-lactamide to 5 weight-% in the buffer, they were allowed to react at 30° C. The DL-lactamide present and the lactic acid formed were monitored with time by HPLC. The results are shown in FIG. 1. In the reaction for 8 hours, D-lactic acid (96% e.e.) was formed in almost 100 mole-% yield from D-lactamide, and almost 100 mole-% L-lactamide remained. Their optical purity was analyzed by Chiralpak WH column supplied by Daicel Chemical Industries, Ltd.

Example 4

Pseudomonas putida IFO12996 was cultivated at 30° C. for 48 hours under shaking in the culture medium shown in Example 1. Then, the microorganism was harvested from the culture broth by centrifugation and washed with 0.05M phosphate buffer, pH 7. After the cell concentration and DL-lactamide were adjusted respectively to approx. 10 weight-% and 1 weight-% in the buffer, they were allowed to react at 30° C. The DL-lactamide present and the lactic acid formed were analyzed by HPLC. In the reaction for 15 hours, D-lactic acid (80% e.e.) was formed in almost 100 mole-% yield.

Example 5

Pseudomonas fluorescens IFO3903 was cultivated at 30° C. for 48 hours under shaking in the culture medium shown in Example 1. Then, the microorganism was harvested from the culture broth by centrifugation and washed with 0.05M phosphate buffer, pH 7. After the cell and DL-lactamide concentration were adjusted respectively to approx. 10 weight-% and 1 weight-% in the buffer, they were allowed to react at 30° C. The DL-lactamide present and the lactic acid formed were analyzed by HPLC. In the reaction for 48 hours, D-lactic acid (92% e.e.) was formed in almost 100 mole-% yield from D-lactamide.

Example 6

Acinetobacter sp. MR-2302 strain was cultivated at 30° C. for 48 hours under shaking in the culture medium shown in Example 1. Then, the microorganism was harvested from the culture liquid by centrifugation and washed with 0.05M phosphate buffer, pH 7. After the cell concentration was adjusted to 1 weight-% in terms of dried microorganism and DL-lactamide to 5 weight-% in the buffer, they were allowed to react at 30° C. The DL-lactamide present and the lactic acid formed were analyzed by HPLC. In the reaction for 6 hours, D-lactic acid (96% e.e.) and L-lactamide were obtained respectively in almost 100 mole-% yield from each of D-lactamide and L-lactamide. Their optical activity was analyzed through Sumichiral OA-5000 column supplied by Sumika Chemical Analysis Service, Ltd.

Example 7

Each strain of Agrobacterium tumefaciens IAM1037, Agrobacterium tumefaciens ATCC4720, Agrobacterium radiobacter IFO12607, Agrobacterium radiobacter IAM1526, Brevibacterium ammoniagenes IFO12072, Brevibacterium ammoniagenes IAM1645, Corynebacterium nitrilophilus ATCC21419, Enterobacter cloacae IFO3320, Micrococcus varians IAM1099, Micrococcus luteus IFO12708, Rhodococcus equi IFO3730, Rhodococcus equi IFM152, Rhodococcus erythropolis IFM155, Rhodococcus erythropolis IFO12320, Rhodococcus erythropolis IFO12538 and Rhodococcus rhodnii IFM148 was cultured at 30° C. for 48 hours under shaking in the culture medium shown in Example 1. Each microorganism was harvested from the culture broth by centrifugation and washed with 0.05M phosphate buffer, pH 7. After the cell concentration and DL-lactamide were adjusted respectively to 10 weight-% and 1 weight-% in the buffer, they were allowed to react at 30° C. The lactic acid formed was analyzed by high performance liquid chromatography (HPLC). The results of the 24-hours reaction are shown in Table 1.

TABLE 1

| Bacterial Strain | Production (weight-%) | Optical Purity of D-isomer (% e.e.) |
| --- | --- | --- |
| Agrobacterium tumefaciens IAM1037 | 0.48 | 94% |
| Agrobacterium tumefaciens ATCC4720 | 0.22 | 97% |
| Agrobacterium radiobacter IFO12607 | 0.28 | 78% |
| Agrobacterium radiobacter IAM1526 | 0.20 | 91% |
| Brevibacterium ammoniagenes IFO12072 | 0.58 | 56% |
| Brevibacterium ammoniagenes IAM1645 | 0.48 | 34% |
| Corynebacterium nitrilophilus ATCC21419 | 0.74 | 32% |
| Enterobacter cloacae IFO3320 | 0.04 | 100% |
| Micrococcus varians IAM1099 | 0.02 | 100% |
| Micrococcus luteus IFO12708 | 0.02 | 100% |
| Rhodococcus equi IFO3730 | 0.60 | 80% |
| Rhodococcus equi IFM152 | 0.06 | 51% |
| Rhodococcus erythropolis IFM155 | 0.52 | 70% |
| Rhodococcus erythropolis IFO12320 | 0.03 | 100% |
| Rhodococcus erythropolis IFO12538 | 0.14 | 60% |
| Rhodococcus rhodnii IFM148 | 0.04 | 100% |

Example 8

Pseudomonas sp. MR-2301 strain was cultivated at 30° C. for 48 hours under shaking in the culture medium shown in Example 1. Then, the microorganism was harvested from the culture broth by centrifugation and washed with 0.05M phosphate buffer, pH 7, to give 30 g of the microorganism (water content of 87.9%) which was then frozen. Separately, 8 g of acrylamide and 0.4 g of methylene- bis-acrylamide were dissolved in 10 g of physiological saline, and this solution was added to 30 g of the above microorganism, followed by being sufficiently mixed in a mixer. To 48 g of the mixture were added 1 g of 25 weight-% aq. glutaraldehyde, 5 g of 5 weight-% aq. dimethylaminopropionitrile and 5 g of 2.5 weight-% aq. potassium persulfate, and the mixture was sufficiently stirred under a nitrogen atmosphere and subjected to polymerization at 5° C. for approx. 2 hours. After the conclusion of the reaction, the resulting polymer was crushed on a wire screen of 10 mesh size. The disrupted polymer passing through this mesh was washed with 0.05M phosphate buffer, pH 7, whereby the moistened immobilized microorganism was obtained.

10 g of the immobilized microorganism was suspended in 180 g of ion-exchanged water. 10 g of DL-lactamide was added thereto and subjected to asymmetric hydrolysis at 30° C. for 24 hours. After the conclusion of the reaction, the immobilized microorganism was recovered by means of a wire screen of 60 mesh size and subjected repeatedly to asymmetric hydrolysis under the same conditions as described above, and the D-lactic acid formed in each reaction was analyzed. The results are shown in Table 2 where the reaction product D-lactic acid was quantitatively determined by HPLC.

Comparative Example 1

The formation of D-lactic acid was examined in the same manner as in Example 8 except that no glutaraldehyde was added. The results are shown in Table 2.

As is evident from Table 2, the durability of the enzyme activity is significantly superior where the enzyme was crosslinked by glutaraldehyde.

TABLE 2

| Number of repeated runs | D-Lactic Acid Formed (%) | |
|---|---|---|
| | Example 8[1] | Comparative Example 1 |
| 1 | 100 | 100 |
| 2 | 98 | 23 |
| 3 | 97 | 8 |
| 5 | 96 | 4 |
| 10 | 94 | — |
| 15 | 92 | — |

[1]The numerical values are expressed in percentage relative to the amount of the D-lactic acid formed in the first asymmetric hydrolysis.

Example 9

450 g of the same frozen microorganism (water content of 80 weight-%) as in Example 8 was thawed and suspended in 150 g of 0.05 M phosphate buffer, pH 7, and 312 g of 27.5 weight-% monomer mixture [acrylamide/N,N'-methylene-bis-acrylamide/dimethylaminoethyl methacrylate contained in the ratio of 10/1/1 by weight in 0.05M phosphate buffer, pH 7.0]and 88 g of 5 weight-% aq. dimethylaminopropionitrile as the polymerization promoter were added thereto. They were sufficiently mixed in a mixer to give 1000 g of a microorganism/monomer mixture solution.

To 1,000 g of the mixture were added a varying amount of from 0.1 to 16 g of 25 weight-% aq. glutaraldehyde and 11 g of 5 weight-% aq. potassium persulfate, and the mixture was stirred at 5° C. under a nitrogen atmosphere. After mixed, the sample formed a gel in about 20 seconds by polymerization under cooling on ice with the center of the polymer being kept at 30° C. or less.

After the conclusion of the reaction, the polymer was allowed to stand overnight at 5° C. and then crushed by being extruded through a wire mesh of 10 mesh size. The disrupted sample was added to 500 ml of 0.05M phosphate buffer, pH 7, and washed by being gently stirred for 1 hour. This sample suspension was separated into the solids and liquid by passing it through a wire mesh of 60 mesh size whereby the granular immobilized microorganism was obtained. The resulting immobilized microorganism was examined on the influence of a varying amount of glutaraldehyde on the leakage of the enzyme from the immobilized microorganism. In the enzyme leakage test, 10 g of the moistened immobilized microorganism was examined for its activity before and after being washed for 15 days at 25in 100 ml of 0.05M phosphate buffer, pH 7.

For the measurement of the enzyme activity, 10 g of the immobilized microorganism was suspended in 180 g of ion-exchanged water, and its activity was then determined in terms of the D-lactic acid formed in the asymmetric hydrolysis of 10 g DL-lactamide at pH 7 and 30for 1 hour. The results are shown in Table 3. As is evident from Table 3, the immobilized microorganism excellent in anti-leakage can be obtained by the use of glutaraldehyde in the range of 0.01–0.25 part relative to 1 part of the microorganism by weight.

TABLE 3

| charging ratio (glutaraldehyde/ microorganism) | activity before and after washing | | evaluation[2] |
|---|---|---|---|
| | 0 day | 15 days[1] | |
| 0.0028/1.0 | 100 | 42 | x |
| 0.014/1.0 | 100 | 87 | Δ |
| 0.028/1.0 | 100 | 89 | o |
| 0.055/1.0 | 100 | 93 | o |
| 0.11/1.0 | 100 | 98 | o |
| 0.165/1.0 | 100 | 96 | o |
| 0.220/1.0 | 100 | 99 | o |
| 0.440/1.0 | —[3] | — | x |

[1]The numerical numbers are expressed in percentage relative to the amount of the D-lactic acid formed by the immobilized microorganism before washing.
[2]o: excellent, Δ: usable, x: not usable.
[3]The gel was too soft to be measured.

Example 10

150 g of the same frozen microorganism (water content of 80 weight-%) as in Example 8 was thawed and suspended in 150 g of 0.05M phosphate buffer, pH 7, followed by addition of the same monomer mixture solution as in Example 8 and 50 weight-% aq. dimethylaminopropionitrile in the ratio of 1: 0.3 by weight. They were sufficiently mixed in a mixer whereby 6 kinds of microorganism/monomer mixture solutions as set forth in Table 4 were prepared.

To each microorganism/monomer mixture solution was added 0.11 part of 25 weight-% aq. glutaraldehyde relative to 1 part of the microorganism by weight, followed by addition of 0.35 part of 5 weight-% aq. potassium persulfate relative to 1 part of the microorganism/monomer mixture solution by weight. They were mixed and polymerized in the same manner as in Example 9.

For the evaluation of the influence of a varying amount of the monomer on the leakage of the enzyme, the resulting polymer was examined in the same manner as in Example 9. The results are shown in Table 4. As is evident from Table 4, the immobilized microorganism excellent in anti-leakage can be obtained by the use of the monomer (entrapping material) in the range of 0.5–10 parts relative to 1 part of the microorganism by weight.

TABLE 4

| charging ratio (monomer/microorganism) | activity before and after washing | | evaluation[2] |
|---|---|---|---|
| | 0 day | 15 days[1] | |
| 15.2/1.0 | 100 | 90 | Δ |
| 8.18/1.0 | 100 | 97 | o |
| 1.884/1.0 | 100 | 95 | o |

TABLE 4-continued

| charging ratio (monomer/microorganism) | activity before and after washing | | evaluation[2] |
|---|---|---|---|
| | 0 day | 15 days[1] | |
| 0.994/1.0 | 100 | 97 | ○ |
| 0.442/1.0 | 100 | 85 | Δ |
| 0.15/1.0 | —[3] | — | × |

[1]The numerical numbers are expressed in percentage relative to the amount of the D-lactic acid formed by the immobilized microorganism before washing.
[2]○: excellent, Δ: usable, ×: not usable.
[3]The gel was too soft to be measured.

Example 11

Pseudomonas sp. MR-2301 strain was cultivated at 30° C. for 48 hours under shaking in the culture medium shown in Example 1. Then, the microorganism was harvested from the culture broth by centrifugation and washed with 0.05M phosphate buffer, pH 7. In the buffer, the cell concentration was adjusted to 2 weight-% in terms of dried microorganism, and DL-lactamide was adjusted to 5, 10, 20, 30, 40 and 50 weight-%, respectively, and they were allowed to react at 30° C.

Figure 2:
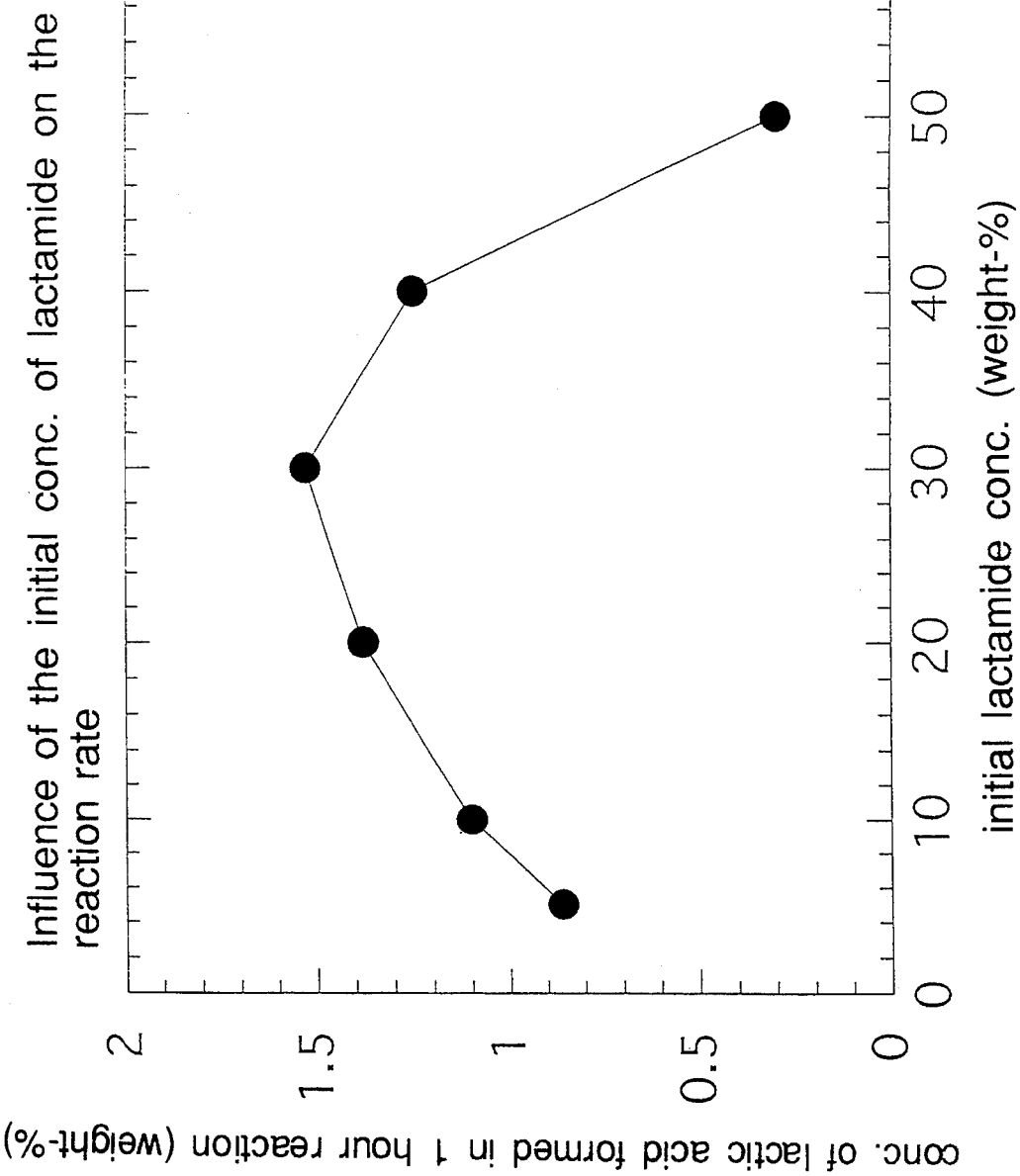
FIG. 2 shows the influence of the initial concentration of the starting material lactamide on the reaction rate.
Figure 3:
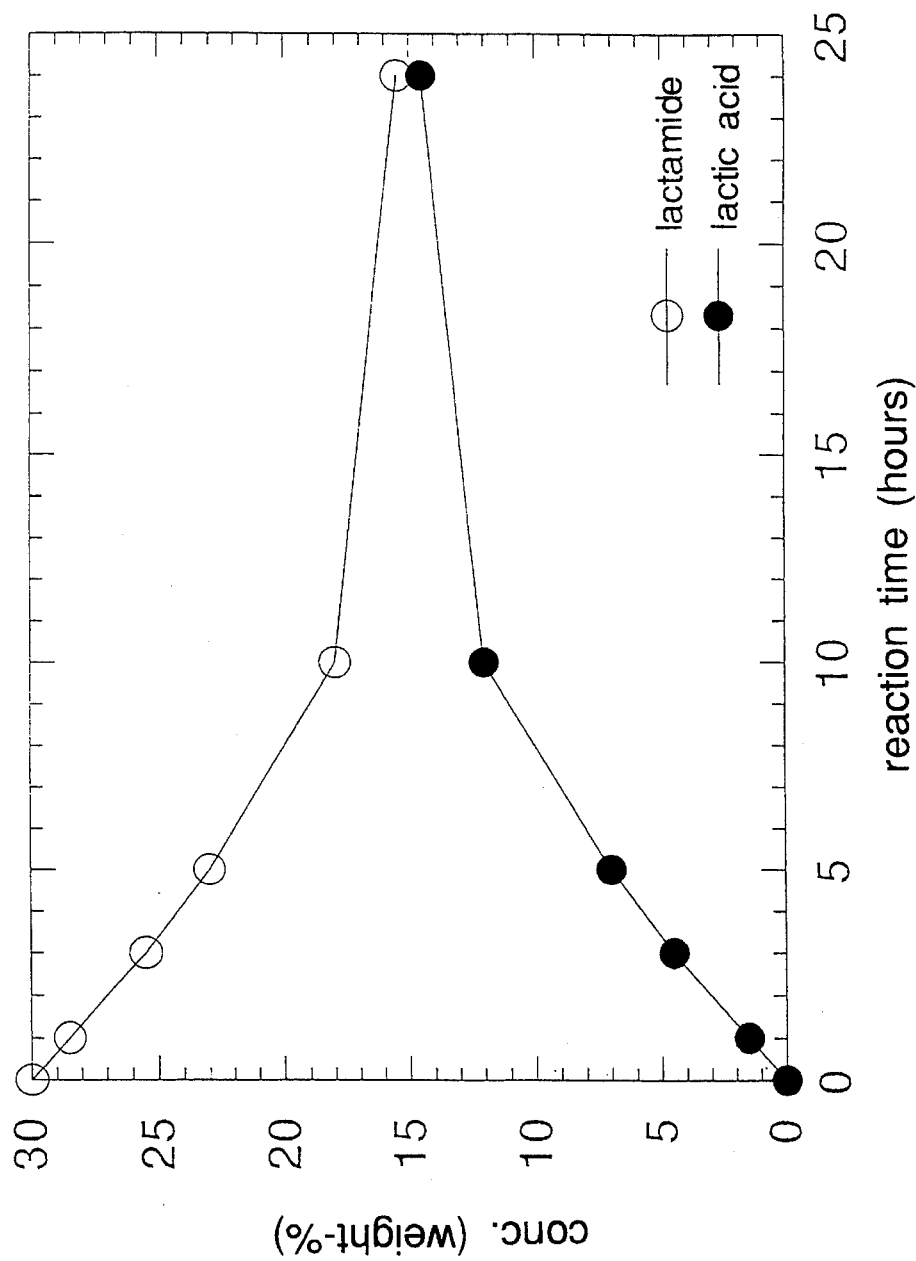
FIG. 3 shows the change with time in the concentrations of lactamide and lactic acid where 30 weight-% lactamide was initially added.
Figure 4:
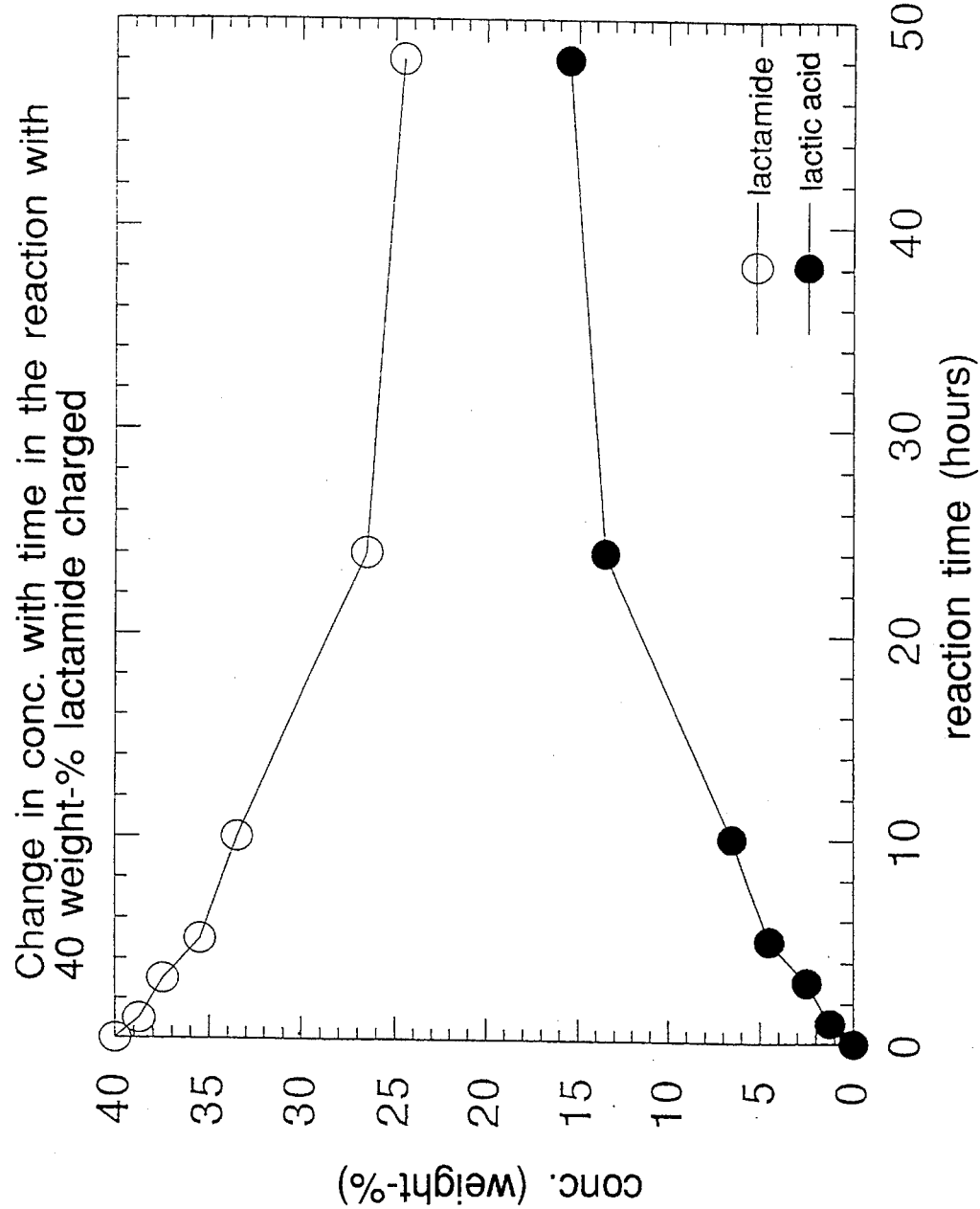
FIG. 4 shows the change with time in the concentrations of lactamide and lactic acid where 40 weight-% lactamide was initially added.
Figure 5:
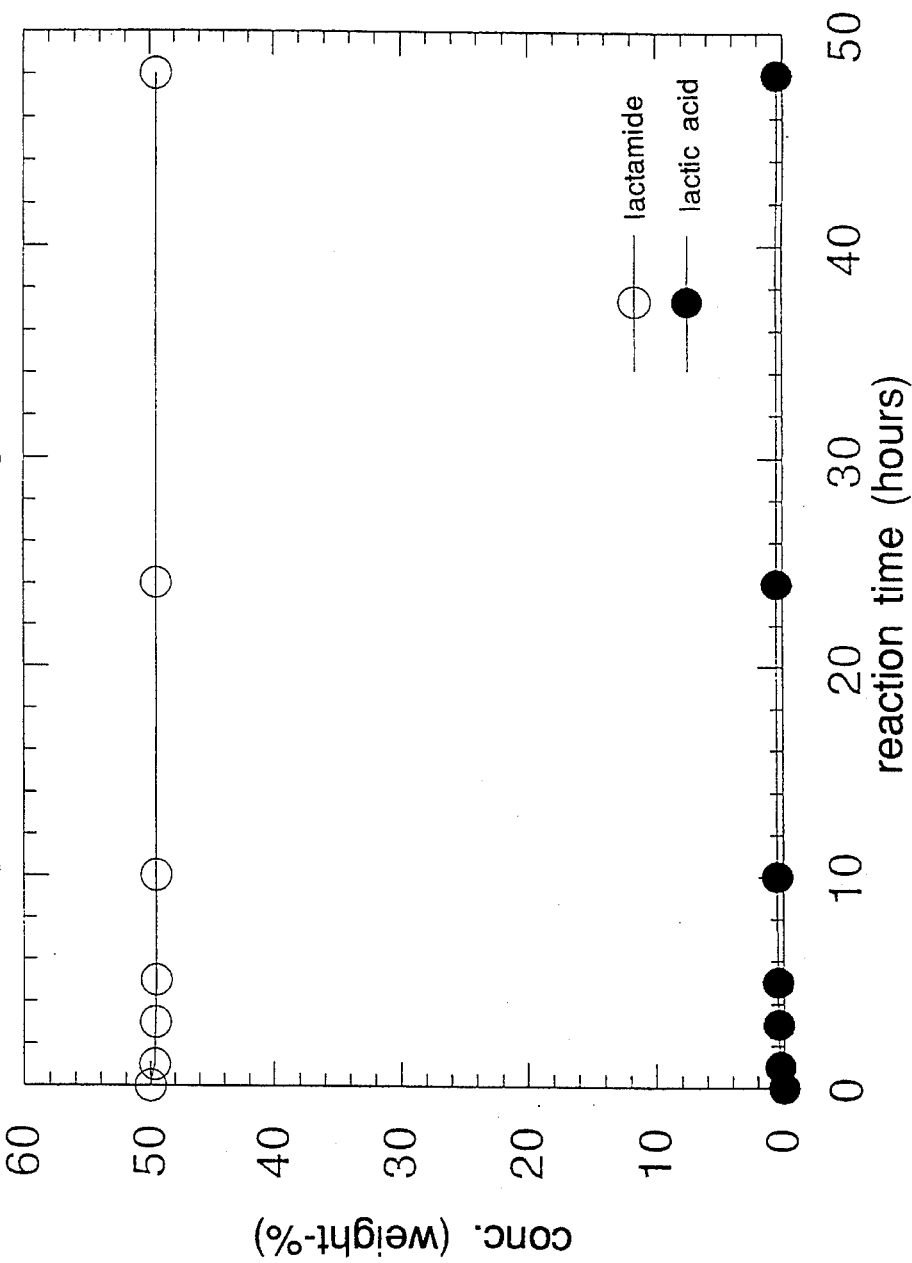
FIG. 5 shows the change with time in the concentrations of lactamide and lactic acid where 50 weight-% lactamide was initially added.

For the examination of the influence of the initial concentration of DL-lactamide on the initial reaction rate, the D-lactic acid formed in the above asymmetric hydrolysis for 1 hour was quantitatively determined by HPLC. FIG. 2 shows the relationship between the initial concentration of DL-lactamide and the amount of the D-lactic acid formed in the reaction for 1 hour. FIGS. 3–5 show the change in the reaction rate with time in the presence of 30, 40 and 50 weight-% lactamide, respectively. The optical purity of the D-lactic acid formed was found to be 96% e.e. by analysis through Chiralpak WH column supplied by Daicel Chemical Industries, Ltd.

As is evident from FIG. 2, the reaction rate was lowered in the presence of an initial concentration of 40 weight-% or more DL-lactamide and significantly lowered in the case of 50 weight-%. As is evident from FIGS. 3 to 5, the accumulability of D-lactic acid was significantly lowered in the presence of an initial concentration of 40 weight-% or more DL-lactamide.

Example 12

Acinetobacter sp. MR-2302 strain was cultivated at 30° C. for 48 hours under shaking in the culture medium shown in Example 1. Then, the microorganism was harvested from the culture broth by centrifugation and washed with 0.05M phosphate buffer, pH 7. In the buffer, the cell concentration was adjusted to 2 weight-% in terms of dried microorganism, and DL-lactamide was adjusted to 20, 30, 40 and 50 weight-%, respectively, and they were allowed to react at 30° C.

For the evaluation of the influence of the initial concentration of DL-lactamide on the initial reaction rate, the D-lactic acid formed in the above asymmetric hydrolysis for 1 hour was quantitatively determined by HPLC. FIG. 6 shows the relationship between the initial concentration of DL-lactamide and the amount of the D-lactic acid formed for 1 hour in the above reaction.

As is evident from FIG. 6, the reaction rate was lowered in the presence of an initial concentration of 40 weight-% or more DL-lactamide and significantly lowered in the case of 50 weight-%.

Example 13

The MR-2301 strain was prepared in the same manner as in Example 1. After the cell concentration was adjusted to 2 weight-% in terms of dried microorganism and DL-lactamide was adjusted to 30 weight-% in phosphate buffer, pH 7.0, they were allowed to react at 30° C. Additional DL-lactamide was added twice (20 hours and 40 hours after the reaction was initiated) to the reaction solution in the ratio of 1: 9 by weight, with the D-lactic acid accumulated being monitored. FIG. 7 shows the relationship with time between the concentration of the D-lactic acid formed and the concentration of the DL-lactamide present. Approx. 25 weight-% lactic acid was accumulated in the reaction for 65 hours.

As is evident from FIG. 7, D-lactic acid can be accumulated at a high concentration in the presence of DL-lactamide controlled in the range of 15–30 weight-%.

The entire disclosure of all references cited and of the Japanese priority applications mentioned in the accompanying Declaration are incorporated herein in their entirety by reference.

We claim:

1. A process for producing D-lactic acid and L-lactamide, comprising the steps of mixing DL-lactamide with an agent selected from the group consisting of a microorganism, a culture broth of a microorganism, a microorganism lysate, and an immobilized microorganism, said microorganism belonging to a genus selected from the group consisting of Alcaligenes, Pseudomonas, Agrobacterium, Brevibacterium, Acinetobacter, Corynebacterium, Enterobacter, Micrococcus and Rhodococcus, wherein the agent catalyses the asymmetric hydrolysis of DL-lactamide to produce a composition comprising D-lactic acid and L-lactamide, and recovering D-lactic acid and L-lactamide from the composition.

2. A process for producing D-lactic acid, comprising the steps of mixing DL-lactamide with an agent selected from the group consisting of a microorganism, a culture broth of a microorganism, a microorganism lysate, and an immobilized microorganism, said microorganism belonging to a genus selected from the group consisting of Alcaligenes, Pseudomonas, Agrobacterium, Brevibacterium, Acinetobacter, Corynebacterium, Enterobacter, Micrococcus and Rhodococcus, wherein the agent catalyses the asymmetric hydrolysis of DL-lactamide to produce a composition comprising D-lactic acid and L-lactamide, and recovering D-lactic acid from the composition.

3. A process for producing L-lactamide, comprising the steps of mixing DL-lactamide with an agent selected form the group consisting of a microorganism, a culture broth of a microorganism, a microorganism lysate, an immobilized microorganism, said microorganism belonging to a genus selected from the group consisting of Alcaligenes, Pseudomonas, Agrobacterium, Brevibacterium, Acinetobacter, Corynebacterium, Enterobacter, Micrococcus and Rhodococcus, wherein the agent catalyses the asymmetric hydrolysis of DL-lactamide to produce a composition comprising D-lactic acid and L-lactamide, and recovering L-lactamide from the composition.

4. A process for producing D-lactic, acid and/or L-lactamide according to claim 1, 2, or 3 wherein said microorganism is selected from the group consisting of Alcaligenes sp. MR-2201 strain (FERM BP4869), Alcaligenes faecalis IFO13111, Pseudomonas sp. MR-2301 strain (FERM BP-4870), *Pseudomonas putida* IFO12996, *Pseudomonas fluorescens* IF03903, *Agrobacterium tumefaciens* IAM1037, Agrobacterium tumefaciens ATCC4720, Agrobacterium radiobacter IFO12607, *Agrobacterium radiobacter* IAM1526, *Brevibacterium ammoniagenes* IFO12072, *Brevibacterium ammoniagenes* IAM1645, Acinetobacter sp. MR-2302 strain (FERM BP-4871), *Corynebacterium nitrilophilus* ATCC21419, *Enterobacter cloacae* IFO3320, *Micrococcus varians* IAM1099, *Micrococcus luteus* IFO12708, *Rhodococcus equi IFO3730*, *Rhodococcus equi* IFM162, *Rhodococcus erythropolis* IFM165, *Rhodococcus erythropolis* IFO12320, *Rhodococcus erythropolis* IFO12538 and Rhodococcus tuber IFM148.

5. A process for producing D-lactic acid and/or L-lactamide according to claim 1 or 3, wherein said microorganisms is a member selected from the group consisting of Alcaligenes sp. MR-2201 strain (FERM BP-4869), Pseudomonas sp. MR-2301 strain (FERM BP-4870) and Acinetobacter sp. MR-2302 strain (FERM BP-4871).

6. A process for producing D-lactic acid and/or L-lactamide according to claim 1, 2, or 3, wherein said agent is an immobilized microorganism prepared by adding a polyfunctional cross-linking agent having aldehyde groups and an entrapping material to the microorganism, followed by polymerization of the entrapping material and the cross-linking agent to form a polymer, and molding the resulting polymer into an arbitrary shape.

7. A process for producing D-lactic acid and/or L-lactamide according to claim 1, 2, or 3 wherein the concentration of DL-lactamide in the process is maintained in the range of 40 weight-% or less during the formation of D-lactic acid and L-lactamide.

8. A process for producing D-lactic acid and/or L-lactamide according to claim 1, 2, or 3, wherein said microorganism is *Rhodococcus erythropolis* IFO12320.

9. A process for producing D-lactic acid and/or L-lactamide according to claim 1, 2, or 3, wherein said microorganism is *Rhodococcus erythropolis* IFO123538.

10. A process for producing D-lactic acid and/or L-lactamide according to claim 1, 2, or 3, wherein said microorganism is *Rhodococcus ruber* IFM148.

11. A process for producing D-lactic acid and/or L-lactamide according to claim 1, 2, or 3, wherein said microorganism is Alcaligenes sp. MR-2201 strain (FERM BP4869).

12. A process for producing D-lactic acid and/or L-lactamide according to claim 1, 2, or 3, wherein said microorganism is Alcaligenes faecalis IFO13111.

13. A process for producing D-lactic acid and/or L-lactamide according to claim 1, 2, or 3, wherein said microorganism is Pseudomonas sp. MR-2301 strain (FERM BP4870).

14. A process for producing D-lactic acid and/or L-lactamide according to claim 1, 2, or 3, wherein said microorganism is *Pseudomonas putida* IFO12996.

15. A process for producing D-lactic acid and/or L-lactamide according to claim 1, 2, or 3, wherein said microorganism is *Pseudomonas fluorescens* IFO3903.

16. A process for producing D-lactic acid and/or L-lactamide according to claim 1, 2, or 3, wherein said microorganism *Agrobacterium tumefaciens* IAM1037.

17. A process for producing D-lactic acid and/or L-lactamide according to claim 1, 2, or 3, wherein said microorganism is *Agrobacterium tumefaciens* ATCC4720.

18. A process for producing D-lactic acid and/or L-lactamide according to claim 1, 2, or 3, wherein said microorganism ms *Agrobacterium radiobacter* IFO12607.

19. A process for producing D-lactic acid and/or L-lactamide according to claim 1, 2, or 3, wherein said microorganism is *Agrobacterium radiobacter* IAM1526.

20. A process for producing D-lactic acid and/or L-lactamide according to claim 1, 2, or 3, wherein said microorganism is *Brevibacterium ammoniagenes* IFO12072.

21. A process for producing D-lactic acid and/or L-lactamide according to claim 1, 2, or 3, wherein said microorganism is *Brevibacterium ammoniagenes* IAM1645.

22. A process for producing D-lactic acid and/or L-lactamide according to claim 1, 2, or 3, wherein said microorganism ms Acinetobacter sp. MR-2302 strain (FERM BP-4871).

23. A process for producing D-lactic acid and/or L-lactamide according to claim 1, 2, or 3, wherein said microorganism is *Corynebacterium nitrilophilus* ATCC21419.

24. A process for producing D-lactic acid and/or L-lactamide according to claim 1, 2, or 3, wherein said microorganism is *Enterobacter cloacae* IFO3320.

25. A process for producing D-lactic acid and/or L-lactamide according to claim 1, 2, or 3, wherein said microorganism is *Micrococcus varians* IAM1099.

26. A process for producing D-lactic acid and/or L-lactamide according to claim 1, 2, or 3, wherein said microorganism is *Micrococcus luteus* IFO12708.

27. A process for producing D-lactic acid and/or L-lactamide according to claim 1, 2, or 3, wherein said microorganism is *Rhodococcus equi* IFO3730.

28. A process for producing D-lactic acid and/or L-lactamide according to claim 1, 2, or 3, wherein said microorganism is *Rhodococcus equi* IFM162.

29. A process for producing D-lactic acid and/or L-lactamide according to claim 1, 2, or 3, wherein said microorganism is *Rhodococcus erythropolis* IFM165.

\* \* \* \* \*